United States Patent [19]

Iida et al.

[11] Patent Number: 4,900,423
[45] Date of Patent: Feb. 13, 1990

[54] ENZYME SENSOR USING IMMOBILIZED GLUCOKINASE

[75] Inventors: Takeaki Iida, Niiza; Takeshi Kawabe, Sumida, both of Japan

[73] Assignee: Unitika Ltd., Hygo, Japan

[21] Appl. No.: 212,104

[22] Filed: Jun. 24, 1988

Related U.S. Application Data

[63] Continuation of Ser. No. 32,719, Apr. 1, 1987, abandoned.

[30] Foreign Application Priority Data

Apr. 2, 1986 [JP] Japan .................... 61-76127

[51] Int. Cl.$^4$ .......................... C12Q 1/00; C12Q 1/54
[52] U.S. Cl. ...................... 204/403; 357/25; 435/4; 435/288; 435/817
[58] Field of Search ............... 204/1 E, 403; 435/291, 435/817, 4, 288; 357/25

[56] References Cited

U.S. PATENT DOCUMENTS

| 4,020,830 | 5/1977 | Johnson et al. | 204/403 X |
| 4,657,854 | 4/1987 | Wegfahrt | 435/14 |

FOREIGN PATENT DOCUMENTS

| 0043181 | 1/1982 | European Pat. Off. | 435/4 |
| 0125136 | 11/1984 | European Pat. Off. | |
| 1598067 | 3/1970 | Fed. Rep. of Germany | |
| 2314498 | 1/1977 | France | |
| 2455279 | 11/1980 | France | |
| 142973 | 7/1980 | German Democratic Rep. | 435/4 |

OTHER PUBLICATIONS

M. Y. Kamel et al., Analytical Biochemistry, 18, 270-273 (1967).
Patent Abstracts of Japan, vol. 10, No. 308 10-21-86, Mitsubishi Electric Corp. abst. & JPA 61122560.
Chemical Abstracts, vol. 95, p. 304 #2947z 1981, "Determination of Adenosine Triphosphate with an Enzyme Electrode", J. Kulys et al. Columbus, OH.

Primary Examiner—G. L. Kaplan
Attorney, Agent, or Firm—Wenderoth, Lind & Ponack

[57] ABSTRACT

An enzyme sensor comprising an enzyme acting specifically on a substrate and a transducer for converting the quantitative change of a substance or heat which is produced or consumed during an enzyme reaction to an electrical signal, wherein the enzyme is glucokinase is disclosed. By the enzyme sensor of the present invention, an accurate determination of an amount of glucose in a sample is possible as well as an accurate determination of adenosine-5'-triphosphate (ATP). A response time of the sensor is almost constant after a long-term use and a decrease of the detecting ratio is very small.

4 Claims, 2 Drawing Sheets

ENZYME SENSOR USING IMMOBILIZED GLUCOKINASE

This application is a continuation of now abandoned application Ser. No. 032,719, filed Apr. 1, 1987.

FIELD OF THE INVENTION

The present invention relates to an enzyme sensor used for determing a concentration of glucose, adenosine-5'-triphosphate (ATP) and the like in a sample.

BACKGROUND OF THE INVENTION

An enzyme sensor, which can quickly and easily determine a concentration of a component to be determined, generally comprises an enzyme for selectively identifying a specific chemical substance such as a molecule and an ion, and a transducer for measuring quantitative change of a substance or heat which is produced or consumed during an enzyme reaction. The transducer, which employs an electrochemical device such as a gas electrode or an ion selective electrode, is mostly used in the field of a clinical chemical examination and a food industry. According to the requirements of miniaturization and integration of enzyme sensors in various fields, a transducer using a semiconductor device, especially an ionsensitive fieldeffect transistor (ISFET), becomes noteworthy. Further, as described in P 246 and 285 of a special feature of enzyme sensors (p. 245–p. 298) in Protein, Nucleic Acid and Enzyme, Vol 30, No. 4, an enzyme sensor employing as a transducer a thermistor working for a heat-measurement is also proposed.

Most of studies in the field of the enzyme sensors have been involved in an enzyme sensor for determining glucose. The enzyme sensors using the transducer as an electrochemical device, a semiconductor device or a heat-measurement device have been also studied. As the enzyme sensor for determining glucose which employs the electrochemical device, it is proposed that glucose oxidase is adopted as an enzyme. This type of sensor utilizes a reaction system in which glucose is changed to hydrogen peroxide and gluconic lactone with consuming oxygen due to an action of glucose oxidase. The enzyme sensor using this reaction is classified into two types. One is the enzyme sensor detecting amounts of consumed oxygen which is in proportion to the concentration of glucose in a sample, with an oxygen electrode. The other is the enzyme sensor detecting amounts of produced hydrogen peroxide which is also in proportion to the concentration of glucose in a sample, with a hydrogen peroxide electrode. It is also known that an amount of oxygen or hydrogen peroxide is determined using an ISFET. In addition to the above mentioned reaction, another reaction system in which glucose is reacted with adenosine-5'-triphosphate (ATP) due to an action of hexokinase to produce glucose-6-phosphate and adenosine-5'-diphosphate (ADP) is also utilized. The enzyme sensor utilizing this reaction system employs as a transducer a heat-measurement device determining amounts of heat produced during the reaction (see Analytical Chemistry, Vol. 47, No. 6, p. 786 to p. 790).

An enzyme sensor for determining adenosine-5'-triphosphate (ATP) employs glucose oxidase and hexokinase as enzymes (EP-OS 125136 corresponding to Japanese Pat. Publication (unexamined) No. 17347/1985). According to this sensor, the reaction of glucose oxidase and glucose is existent with the reaction of hexokinase and glucose and then a ratio of both reactions is changed depending on an amount of adenosine-5'-triphosphate (ATP). Another enzyme sensor for determining adenosine-5'-triphosphate (ATP) employs adenosine-5'-triphosphate hydrolase (AT Pase) with which adenosine-5'-triphosphate (ATP) is hydrolyzed to produce hydrogen ions (see the Gists of Lectures, p. 604 (1985), the 50th Annual Meeting in spring of the Chemical Society of Japan; the Gists of Lectures F-4, p. 7, the 52th Annual Meeting of Electrochemical Society of Japan). In this sensor, the pH change is measured by an ISFET.

Among the above mentioned sensors, a sensor employing glucose oxidase has a long response time because of the lack of oxygen dissolved in a solution. In a sensor employing an oxygen electrode, hydrogen peroxide is also decomposed during the measurement to oxygen and hydrogen oxide. The decomposed oxygen is also detected by the oxygen electrode to causes a measurement error. In the sensor using a hydrogen peroxide electrode, reductive materials in a sample disturb a correct measurement. In case of the sensor employing hexokinase, hexokinase can be effective not only on glucose but also on mannose and fructose to cause preventing a proper measurement. The sensors mentioned above also have a long response time if they are kept without using for a long time and become poor in detecting ratio. Further, if they are repeatedly used, a decline of determining properties becomes significant. In the sensor using adenosine-5'-triphosphate hydrolase (AT Pase), the activity of adenosine-5'-triphosphate hydrolase (AT Pase) loses in a short time and a detecting range is very small.

SUMMARY OF THE INVENTION

An object of the present invention is to provide an enzyme sensor which selectively determines an amount of glucose or adenosine-5'-triphosphate (ATP) and endures long-term use without the decline of determining properties.

After intensely studying in order to accomplish the above mentioned object, the inventors of the present invention have found that an enzyme sensor, in which glucokinase is used as an enzyme, does not prolong a response time in long-term use and does not lower a detecting ratio. Accordingly, the present invention is to provide an enzyme sensor comprising an enzyme acting specifically to a substrate and a transducer for converting the quantitative change of a substance or heat which is produced or consumed during an enzyme reaction to an electrical signal, wherein the enzyme is glucokinase.

According to the enzyme sensor of the present invention, an accurate determination of an amount of ATP in a sample is possible as well as an accurate determination of glucose. A response time of the sensor is almost constant after a long-term use and a decrease of the detecting ratio is very small.

DETAILED DESCRIPTION OF THE INVENTION

Figure 1:
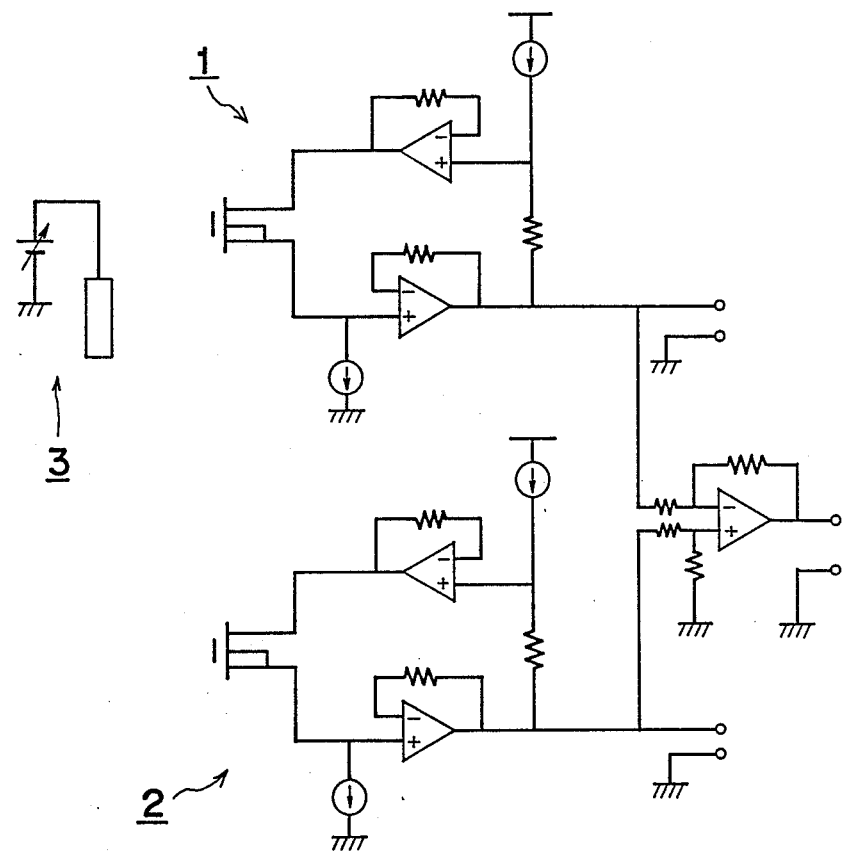
FIG. 1 shows a circuit drawing comprising an ionsensitive fieldeffect transistor (ISFET) 1 on which glucokinase is immobilized, an ionsensitive fieldeffect transistor (ISFET) 2 on which glucokinase is not immobilized and an Ag/AgCl electrode 3.

The transducer employed in the present invention includes an electrochemical device, a semiconductor device or a heat-measurement device. Preferred are the semiconductor device such as an ionsensitive fieldeffect transistor (ISFET), which can be miniaturized and easily integrated.

Glucokinase employed in the present invention is not limited in supply sources and may be those derived from microorganisms or those derived from animals. Preferred are those produced from microorganisms which most suitable growth temperature is in a range of 50° to 85° C. Examples of the microorganisms are Bacillus sp. such as *Bacillus stearothermophilus, Bacillus thermoproteolyticus, Bacillus acidocaldarius;* Thermoactinomyces sp.; Thermus sp.; Thermomicrobium sp. and the like. Typical examples of the microorganisms are *Bacillus stearothermophilus,* of which specific examples are ATCC 7933 strain (ATCC: The American Type Culture Collection, Maryland, U.S.A.), ATCC 7954 strain, ATCC 10194 strain, ATCC 12980 strain, NCA 1503 strain (NCA; National Canners' Association, Washington, D.C., U.S.A.), UK 563 strain (PERM P-7275 strain, deposited at Fermentation Research Institute, Agency of Industrial Science and Technology, Ibaragi, Japan, on Sept. 29, 1983) and the like.

Glucokinase used in the present invention is generally immobilized on a water-insoluble carrier having a membrane shape, a particle shape, a fiber shape, a hollow fiber shape, a tube shape and the like. The water-insoluble carrier on which glucokinase is immobilized may be put into various type reaction vessels, i.e. stirring type, packing type, flow type, tube type and the like, and incorporated into a flow system, whereby an output flow is led to a sensitive surface of the electrode. The water-insoluble carrier having a membrane shape, on which glucokinase is immobilized, may directly cover the sensitive surface of the electrode. The latter process in which the sensitive surface of the electrode is covered by a glucokinase membrane is preferred from th aspect of the miniaturization and integration of the enzyme sensor. In the latter process, a thickness of the glucokinase membrane is, for example, 1 to 100 micron, preferably 10 to 50 micron.

The immobilization of glucokinase to the water-insoluble carrier can be carried out by a covalent bond method or an absorbed method, which are conventionally known as described in "Immobilized Enzyme" by Ichiro, CHIBATA, Kodan-sha (1975). It can also be carried out by a crosslinking method or an entrapped method. The covalent bond method includes a peptide bond method, in which CNBr-activated agarose or dextran is bonded with an amino group of glucokinase: a diazo method, in which a water-insoluble carrier having an aromatic amino group is changed by a nitrite to a diazonium salt to which tyrosine residues of glucokinase are coupled: a Schiff base method, in which a water-insoluble carrier having an amino group is bonded with glutaraldehyde and then to which an amino group of glucokinase is bonded: a method, in which a porous glass, silica, or metal oxide is aminosilanized by gamma-aminopropyltriethoxysilane and treated with glutaraldehyde and then bonded with an amino group of glucokinase; and the like. The absorbed method includes a method in which glucokinase is immobilized on a water-insoluble carrier, such as DEAE-cellulose or phenoxyacetylcellulose and the like, with an ion bond or a physical force. The crosslinking method includes a method in which glucokinase and an amino group of albumin are crosslinked by glutaraldehyde to immobilize glucokinase on albumin. The entrapped method includes a method, in which a solution containing acrylamide monomers, a crosslinking agent. ( e.g. N,N'-methylenebisacrylamide), an initiator (e.g. riboflavin and peroxodisulfate), and a polymerization promoter (e.g. N,N,N',N'-tetramethylethylenediamine) is added to a glucokinase solution and polymerized with light under a nitrogen blanket; a method in which glucokinase is added to a collagenfibril suspension and dried after pouring it on a Teflon board: a method in which two platinum electrodes are inserted in a suspension containing collagen and glucokinase and a direct current voltage is applied to form a collagen membrane containing glucokinase on the cathode; and the like.

For determining an amount of glucose by using the enzyme sensor of the present invention, a buffer solution containing a magnesium salt and adenosine-5'-triphosphate (ATP) may be passed through a reaction vessel including the immobilized glucokinase, of which an output solution is detected by the transducer. In this case, a change of a detecting substance which is produced by adding a glucose solution is determined by the enzyme sensor. Also, the sensitive surface of the transducer covered by the immobilized glucokinase is immersed in the buffer solution containing a magnesium salt and adenosine-5'-triphosphate (ATP) and a change of a detecting substance which is produced by adding a glucose solution may be determined by the enzyme sensor. In this case, a pH change of H+ produced by the following reaction is detected by a pH electrode or an ionsensitive field effect transistor (ISFET):

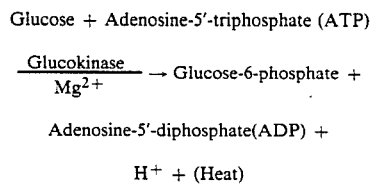

Glucose + Adenosine-5'-triphosphate (ATP)

$$\xrightarrow[Mg^{2+}]{Glucokinase} \text{Glucose-6-phosphate} +$$

Adenosine-5'-diphosphate(ADP) +

H+ + (Heat)

Also, change of heat may be detected by a thermistor. It is preferred that pH change due to H+ is detected by the pH electrode or the ionsensitive field effect transistor (ISFET).

The preferred buffer solution for the determination contains 0.1 to 20 mM, preferably 0.3 to 5 mM of adenosine-5'-triphosphate (ATP), and 0.5 to 50 mM, preferably 2 to 30 mM of a magnesium salt. The buffer solution is prepared by dissolving adenosine-5'-triphosphate (ATP) and the magnesium salt in a buffer solution (pH 4 to 10, preferably pH 5.5 to 9.5), such as Tris-hydrochloric acid, imidazole acetic acid and the like.

Determination of adenosine-5'-triphosphate (ATP) is carried out by employing glucose instead of the ATP in the buffer solution. In this case, an amount of glucose is 0.1 to 30 mM, preferably 0.8 to 15 mM in the buffer solution.

A temperature for the determination of the present invention is within a range of 5° to 75° C., preferably 15° to 55° C.

EXAMPLES

The present invention is illustrated by the following examples, which, however, are not to be construed as limiting the present invention to their details.

EXAMPLE 1 and COMPARATIVE EXAMPLES 1 and 2

20 μl (23 units) of glucokinase derived from *Bacillus stearothermophilus* were mixed with 2 μl of 25 W/V % bovin serum albumin. 2 μl of the obtained mixture was added dropwise on a gate of an ionsensitive field effect transistor (ISFET) and air-dried at room temperature for 20 minutes. 2 μof 1 W/V-% glutaraldehyde was added dropwise on the gate and reacted at 4° C. for a whole day and night to form an immobilized membrane. This was immersed into a 0.1 M glycine-sodium hydroxide buffer solution at pH 8.5 for 15 minutes and rinsed with distilled water to obtain an ionsensitive field effect transistor (ISFET) on which glucokinase was immobilized.

The glucokinase immobilized ionsensitive field effect transistor (ISFET) 1 and a non-immobilized ionsensitive field effect transistor (ISFET) 2 for control were immersed in a 25 ml of a reaction solution composed of 20 mM of tris-hydrochloric acid buffer solution (pH9.0), 20 mM of magnesium chloride and 4 mM of adenosine-5'-triphosphate (ATP). An Ag/AgCl electrode was immersed in the reaction solution for fixing a voltage of the solution. The ionsensitive field effect transistors (ISFET) had the circuit shown in FIG. 1, wherein a voltage between source drains of the two ISFETs set at 3.0 and an applied voltage of the Ag/AgCl electrode was 6.5 V. When glucose solution was added into the reaction solution at a boundary surface of the ISFET pH partially changes. The change was detected as a differential output between the two ISFETs. The temperature for the reaction was 30° C. and stirring of the reaction solution was conducted at 200 rpm.

Figure 2:
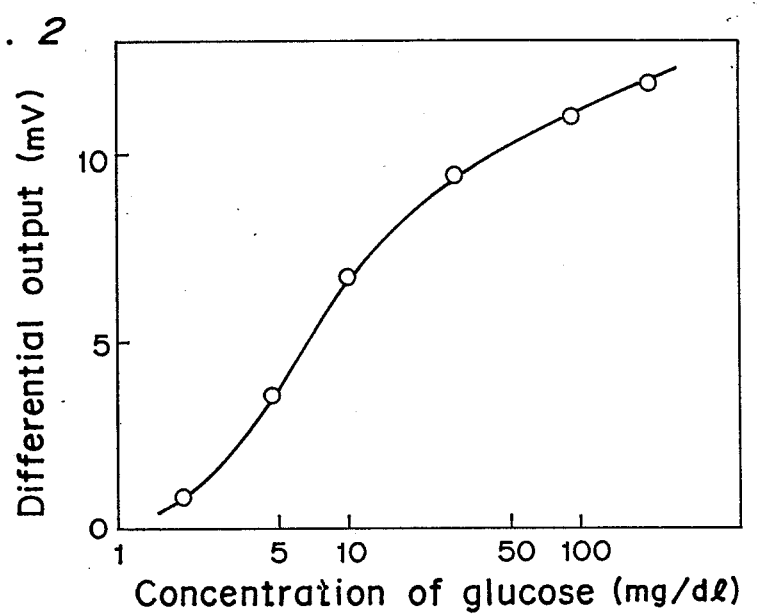
FIG. 2 is a drawing showing a relation between a concentration of glucose and a differential output.

A concentration of the glucose solution was adjusted to 2, 5, 10, 30, 100 and 200 mg/dl and the relation between the glucose concentration and the differential output was shown in FIG. 2. As is apparent from FIG. 2, the enzyme sensor exhibits good response properties in a concentration range of 2 to 200 mg/dl. It has been found that the enzyme sensor of the present invention can effectively determine an amount of glucose.

Next, for testing stability of the enzyme sensor of the present invention in long term determination was carried out using a glucose solution of 10 mg/dl after leaving for one month, 3 months and 6 months at 37° C. The response time and glucose detecting ratio are shown in Table 1.

For a comparison, the same test was made by employing hexokinase derived from yeast instead of glucokinase derived from *Bacillus stearothermophillus*. The result is shown in Table 1 as Comparative Example 1. Another comparison was made by using a commercially available enzyme sensor in which glucose oxidase was immobilized on a hydrogen peroxide electrode. The same test was carried out. The result is shown in Table 1 as Comparative Example 2.

TABLE 1

| | Example | | Comparative Example | | | |
| | | | 1 | | 2 | |
| | Response time (min) | Detecting ratio (%) | Response time (min) | Detecting Ratio (%) | Response time (min) | Detecting ratio (%) |
|---|---|---|---|---|---|---|
| Immediate after preparation or purchase | 2.0 | 100 | 3.0 | 100 | 2.5 | 100 |
| After one month | 2.0 | 100 | 25 | 30 | 12 | 50 |
| After 3 months | 2.3 | 98 | 60 | 5 | 30 | 10 |
| After 6 months | 2.4 | 97 | — | — | — | — |

It is clear from Table 1 that the enzyme sensor of the present invention is very stable in comparison with the other sensors.

For testing the stability of the sensor of the present invention after repeatedly and continuously using, the same test was carried out by using a serum sample containing a glucose concentration of 50 mg/dl after using the sensor 50 times/day for 10, 20 and 30 days. The result is shown in Table 2.

For a comparison, the sensors for Comparative examples were used and the same test was conducted. The result is shown in Table 2.

TABLE 2

| | Example | | Comparative Example | | | |
| | | | 1 | | 2 | |
| | Response time (min) | Detecting ratio (%) | Response time (min) | Detecting Ratio (%) | Response time (min) | Detecting ratio (%) |
|---|---|---|---|---|---|---|
| Immediate after preparation or purchase | 2.0 | 100 | 3.0 | 100 | 2.5 | 100 |
| After 10 days | 2.2 | 99 | 10 | 70 | 7 | 80 |
| After 20 days | 2.4 | 98 | 30 | 30 | 19 | 30 |
| After 30 days | 2.5 | 97 | 60 | 5 | 32 | 8 |

It is clear from Table 2 that the enzyme sensor of the present invention does not deteriorate its quality in comparison with the other sensors.

EXAMPLE 2

A relation between differential outputs and concentrations was obtained as generally described in Example 1 with the exception that 12 mM of glucose was employed instead of 4 mM of adenosine-5'-triphosphate (ATP) and a concentration of the ATP solution was adjusted to 50, 100, 200, 300 and 500 mg/dl was employed instead of the glucose solution.

Figure 3:
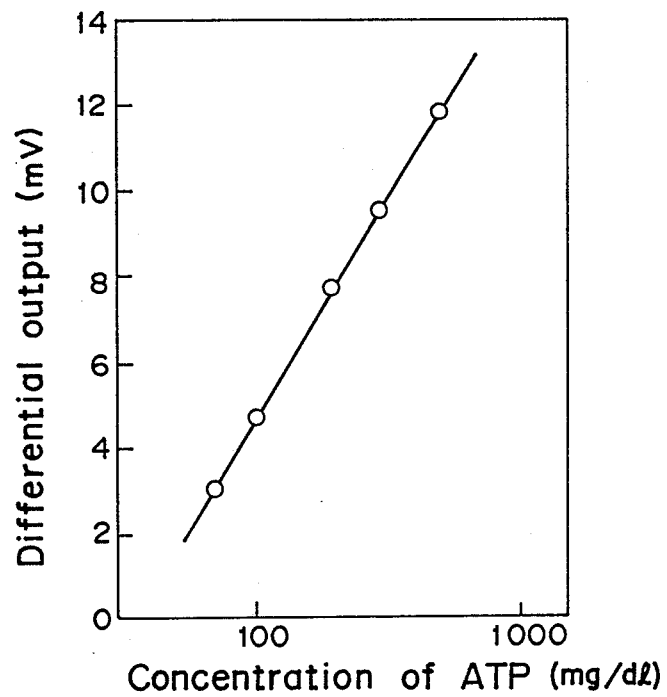
FIG. 3 is a drawing showing a relation between a concentration of adenosine-5'-triphosphate (ATP) and a differential output.

The result is shown in FIG. 3. As is apparent from FIG. 3, the sensor of the present invention has good response properties in a range of 50 to 500 mg/dl and it has been found that the sensor of the present invention can determine adenosine-5'-triphosphate (ATP).

What is claimed is:

1. An enzyme sensor comprising an immobilized glucokinase acting specifically on a substrate and a transducer for converting the quantitative change of hydrogen ions produced or consumed during an enzyme reaction to an electrical signal.

2. The enzyme sensor according to claim 1 wherein said substrate is glucose.

3. The enzyme sensor according to claim 1 wherein said substrate is adenosine-5'-triphosphate (ATP).

4. The enzyme sensor according to claim 1 wherein glucokinase is derived from microorganisms cultured in a temperature range of 50° to 85° C.

* * * * *